United States Patent [19]
Bischoff et al.

[11] Patent Number: 5,843,141
[45] Date of Patent: Dec. 1, 1998

[54] MEDICAL LEAD CONNECTOR SYSTEM

[75] Inventors: Thomas C. Bischoff, Minneapolis; Bonner D. Bonner, Plymouth; Timothy G. Laske, Shoreview; Andrew J. Ries, Circle Pines; John L. Sommer, Coon Rapids, all of Minn.

[73] Assignee: Medronic, Inc., Minneapolis, Minn.

[21] Appl. No.: 846,008

[22] Filed: Apr. 25, 1997

[51] Int. Cl.$^6$ .................................................. A61N 1/372
[52] U.S. Cl. ............................................................. 607/37
[58] Field of Search ................................ 607/37, 38, 119, 607/122, 123, 132; 606/129

[56] References Cited

U.S. PATENT DOCUMENTS

| | | |
|---|---|---|
| 3,649,367 | 3/1972 | Purdy . |
| 4,180,078 | 12/1979 | Anderson . |
| 4,355,646 | 10/1982 | Kallok et al. . |
| 4,469,104 | 9/1984 | Peers-Trevarton . |
| 4,608,986 | 9/1986 | Beranek et al. . |
| 4,860,750 | 8/1989 | Frey et al. . |
| 4,934,367 | 6/1990 | Daglow et al. . |
| 4,971,057 | 11/1990 | Theres . |
| 5,076,270 | 12/1991 | Stutz, Jr. . |
| 5,174,288 | 12/1992 | Bardy et al. . |
| 5,207,218 | 5/1993 | Carpetntier et al. . |
| 5,252,090 | 10/1993 | Giurtino et al. . |
| 5,257,622 | 11/1993 | Hooper et al. . |
| 5,304,219 | 4/1994 | Chernoff et al. . |
| 5,324,321 | 6/1994 | Pohndorf et al. . |
| 5,331,966 | 7/1994 | Bennett et al. . |
| 5,358,517 | 10/1994 | Pohndorf et al. . |
| 5,431,695 | 7/1995 | Wiklund et al. . |
| 5,489,225 | 2/1996 | Julian . |
| 5,514,172 | 5/1996 | Mueller . |
| 5,584,873 | 12/1996 | Shoberg et al. . |

Primary Examiner—William C. Kamm
Attorney, Agent, or Firm—Reed A. Duthler; Harold R. Patton

[57] ABSTRACT

An implantable medical device system including an implantable electronic device having multiple electrical connectors and an associated electrical lead also having a corresponding set of electrical connectors which engage with the connectors on the device. The lead has a connector assembly mounted to its proximal end, including the lead's electrical connectors and a mechanical connector. The device has a connector block with a bore extending therethrough sized to receive the connector assembly of the lead. A pulling tool is provided for pulling the lead connector assembly proximally in the bore of said connector block from a first position in which the lead's connector assembly is not fully inserted in the connector block to a second position in which said connector assembly is fully inserted in the connector block, the pulling tool being provided with a mechanical connector which engages with mechanical connector on the lead's connector assembly.

20 Claims, 11 Drawing Sheets

MEDICAL LEAD CONNECTOR SYSTEM

BACKGROUND OF THE INVENTION

The present invention relates to medical stimulators and leads generally and more particularly to mechanisms for interconnecting implantable medical stimulators and leads.

The mechanisms for connecting implantable electrical leads and implantable stimulators generally have taken the form of a connector block affixed to the implantable stimulator which is provided with a bore for receiving the proximal end of the associated electrical lead. The bore of the connector block typically contains one or more electrical connectors, which engage with one or more connector pins or rings located on a connector assembly at the proximal end of the lead. At present, most implantable devices employ connectors having bores which contain one or two electrical connectors, which receive connector assemblies which correspondingly also are provided with one or two connectors, usually taking the form of a connector pin and a larger diameter connector ring, located distal to the connector pin. One example of such an interconnection system is the IS-1 connector standard commonly in use in conjunction with implantable pacemakers and defibrillators, corresponding generally to the electrical connector systems illustrated in U.S. Pat. No. 5,076,270 issued to Stutz, Jr., U.S. Pat. No. 5,514,172 issued to Mueller and U.S. Pat. No. 5,431,695 issued to Wicklund et al.

As electrical stimulation leads grow more complex, carrying increasing numbers of sensors, electrodes, or other electrical components, the necessity for an increased number of electrical connections to the lead correspondingly arises. Typically, in commercially marketed leads for use with cardiac pacemakers and implantable defibrillators, leads which require more than two interconnections are provided with bifurcated connector assemblies having two arms, each arm carrying one or two connectors. Examples of such bifurcated connector assemblies can be found in U.S. Pat. No. 5,174,288 issued to Bardy et al and U.S. Pat. No. 4,180,078 issued to Anderson. It has been proposed repeatedly that rather than employing bifurcated connector assemblies, it would be more beneficial to employ a lead with more than two connectors arranged linearly along a single, non-bifurcated connector assembly, which in turn could be inserted into a single connector bore on the associated implantable stimulator. Numerous proposals for such multi-polar in-line connector systems have been put forward, as set forth in U.S. Pat. No. 4,934,367 issued to Daglow, U.S. Pat. No. 5,304,219 issued to Chernoff et al., U.S. Pat. No. 4,971,057 issued to Theres and U.S. Pat. No. 4,469,104 issued to Peers Trevarton. However, when implanting such connector systems, certain practical difficulties may arise.

Particularly in the context of implantable defibrillators, it is necessary to have a high degree of electrical isolation between connectors within the same bore of the connector block. It is also necessary to provide for a high degree of resistance to fluid intrusion into the bore. The traditional mechanism for meeting these requirements has been the provision of elastomeric sealing rings, separating adjacent electrical connectors from one another and sealing the entry point of the lead. The sealing rings may be located either on the lead connector assembly or in the connector block. However, each additional set of sealing rings increases the amount of force required to insert the lead connector assembly into the bore of the connector block. Since the lead is normally inserted by pushing the lead connector assembly into the connector block, the portion of the lead immediately distal to portion of the connector assembly that will reside in the bore is normally designed to be stiff enough to allow the required level of insertion force to be applied to the connector assembly. However, increasing the stiffness of the lead at the point it exits from the implantable stimulator complicates design of the lead and is not desirable beyond a certain point, due to the desire that the excess lead may be curved or coiled closely adjacent to pulse generator to minimize the size of the pocket in which the device is implanted.

In most implantable pacemakers and cardioverters, each electrical connection is secured by means of a set screw, as illustrated in the Wicklund et al. patent cited above. However, as the number of the electrical connections increases, the use of toolless connectors, employing frictional forces as interconnection mechanisms becomes correspondingly more desirable. Such mechanisms typically include conductive spring members of some sort which engage the connector pins or rings on the connector assembly of the lead, as illustrated in the Daglow, Peers Trevarton and Stutz Jr. patents cited above. Such frictional interconnection mechanisms, of course, also increases the lorce required to insert the lead, correspondingly increasing the necessary stiffness of the lead distal to the connector assembly.

A corresponding issue associated with increased insertion forces is that the removal force of the lead is correspondingly increased. Since leads are typically removed by means of tension applied to the lead, insertion/removal forces beyond a certain amount require reinforcement of the lead structure, so that the lead is not damaged when removing the lead from the connector block. All of the considerations discussed above complicate the design and manufacture of leads, and are believed in part responsible for the fact that multi-polar in-line connector systems having more than two electrodes are not widely employed in the context of implantable pacemakers and defibrillators.

SUMMARY OF THE INVENTION

The present invention is directed toward providing a practical, multi-polar in-line connector system for use in interconnecting implanted stimulators and associated leads which may workably be employed in conjunction with connector assemblies having three, four or more connectors located in line along a single, non-bifurcated connector assembly inserted within a single connector bore of an implanted stimulator. In addition, the invention is directed toward providing such an interconnection system in a fashion that allows the use of toolless, frictional, compressive electrical connections of the sort described above for most or all of the electrical interconnections between the stimulator and the lead.

The present invention provides these benefits by taking a substantially different approach to the insertion of the lead into the connector block, by means of a mechanism which allows the connector assembly on the lead to be pulled into the connector block bore, rather than being pushed into the connector block bore. The connector block may correspond to any of the connector blocks proposed for multipolar, in-line connectors in the patents cited above, with the additional feature that the bore is open at both ends of the connector block, and means are provided to seal the connector block to the lead at both ends of the connector bore. The connector assembly of the lead may correspond to any of the multi-polar in-line connector assemblies disclosed in the patents cited above, but is additionally provided with means for mechanically interconnecting the proximal end of the connector assembly with a pulling tool. The mechanical interconnection mechanism may be, for example, a threaded bore, formed in the proximal-most portion of the lead connector assembly. The pulling tool is provided with a rod which carries a corresponding interconnection mechanism, for example, a threaded extension, which may engage with the interconnection mechanism on the proximal end of the lead connector assembly. The pulling tool may be provided with a knob on its proximal end to assist in screwing the tool to the lead connector assembly and to assist in pulling the lead into the connector block. In use, the proximal end of the connector assembly on the lead is inserted partially into one end of the bore in the connector block of the stimulator, and the pulling tool is inserted into the opposite end of the bore, and connected to the proximal end of the lead connector assembly. The pulling tool is then used to pull the lead connector assembly into the connector block on the stimulator, until the electrical connectors on the lead connector assembly and in the connector block are aligned with one another. An internal stop surface within the connector block and a visual indicator on the pulling tool assist in assuring proper alignment. The pulling tool is then detached from the lead connector assembly prior to implantation of the stimulator.

In preferred embodiments, the connector block of the stimulator is provided with electrical connections which frictionally engage the connector pins or rings on the lead connector assembly, rather than with more traditional set screw type connectors. The net result of this connector system is a system in which the insertion/removal force of the connector may be adequate to retain the lead within the connector block. However, in some embodiments, a single set screw type connector or other additional mechanical locking mechanism to may be appropriate, if only to alleviate concerns on the part of physicians with regard to the reliability of the mechanical interconnection of the lead and stimulator.

The high insertion force systems carries with it a correspondingly high removal force. The present invention addresses this problem by means of the same pulling tool used to insert the lead, which may be reinserted into the lumen and used to push the lead out of the bore. This mechanism for removing the lead from the stimulator obviates the necessity of providing a lead body having a high tensile strength in the vicinity of the connector assembly. In general, because the lead body is not employed either to overcome substantial insertion or removal forces, the lead body may be designed according to any other set of physical constraints desired by the inventors, simplifying design and construction of the lead. The structure of the lead body may thus be chosen to optimize other lead characteristics such as flexibility and size, which otherwise might be negatively impacted if the lead body had to be capable of applying the required insertion and removal forces. In particular, the lead may be constructed to display a small diameter and a high level of flexibility adjacent to the point at which the lead exits the connector block, allowing the lead to be wrapped closely around or adjacently the implanted stimulator, and reducing the overall pocket volume required to implant the stimulator.

In an alternative embodiment of the lead, the pulling tool is optimized for use in conjunction with a lead intended to be introduced by means of a guide catheter or elongated introducer sheath. In this embodiment, the knob is replaced by an elongated flexible extension which exceeds the length of the guide catheter through which the lead is to be advanced. In this embodiment of the invention, the lead is first advanced through the guide catheter to a desired location. The pulling tool/extension is coupled to the proximal end of the lead connector assembly before or after placement of the lead at the desired location, and the extension is used to maintain the lead in its desired location while the guide catheter is removed by pulling it proximally over the lead body and connector until the distal end of the guide catheter is located proximal to the connector assembly on the lead. At this point, the connector assembly of the lead can then be grasped by the physician, while the guide catheter is pulled off of the extension. Alternatively, the pulling tool/extension may be removed from the lead connector at this point, and discarded along with the guide catheter.

If the pulling tool/extension remains attached to the lead, it may thereafter be employed as a pulling tool for pulling the lead into the connector assembly of the associated stimulator. The extension may be passed intact through the lumen of the connector block on the stimulator, or maybe trimmed to a shorter length, prior to insertion into the bore of the connector block on the stimulator. The pulling tool/ extension is thereafter employed to pull the lead into its correct position within the connector block of the stimulator, and the pulling tool/extension is then removed and discarded. If the pulling tool/extension was previously removed and discarded with the guide catheter, a pulling tool with a knob as described above may be used to insert the lead into the connector block of the associated stimulator.

A BRIEF DESCRIPTION OF THE DRAWINGS

DETAILED DESCRIPTION OF THE PREFERRED EMBODIMENTS

Figure 1:
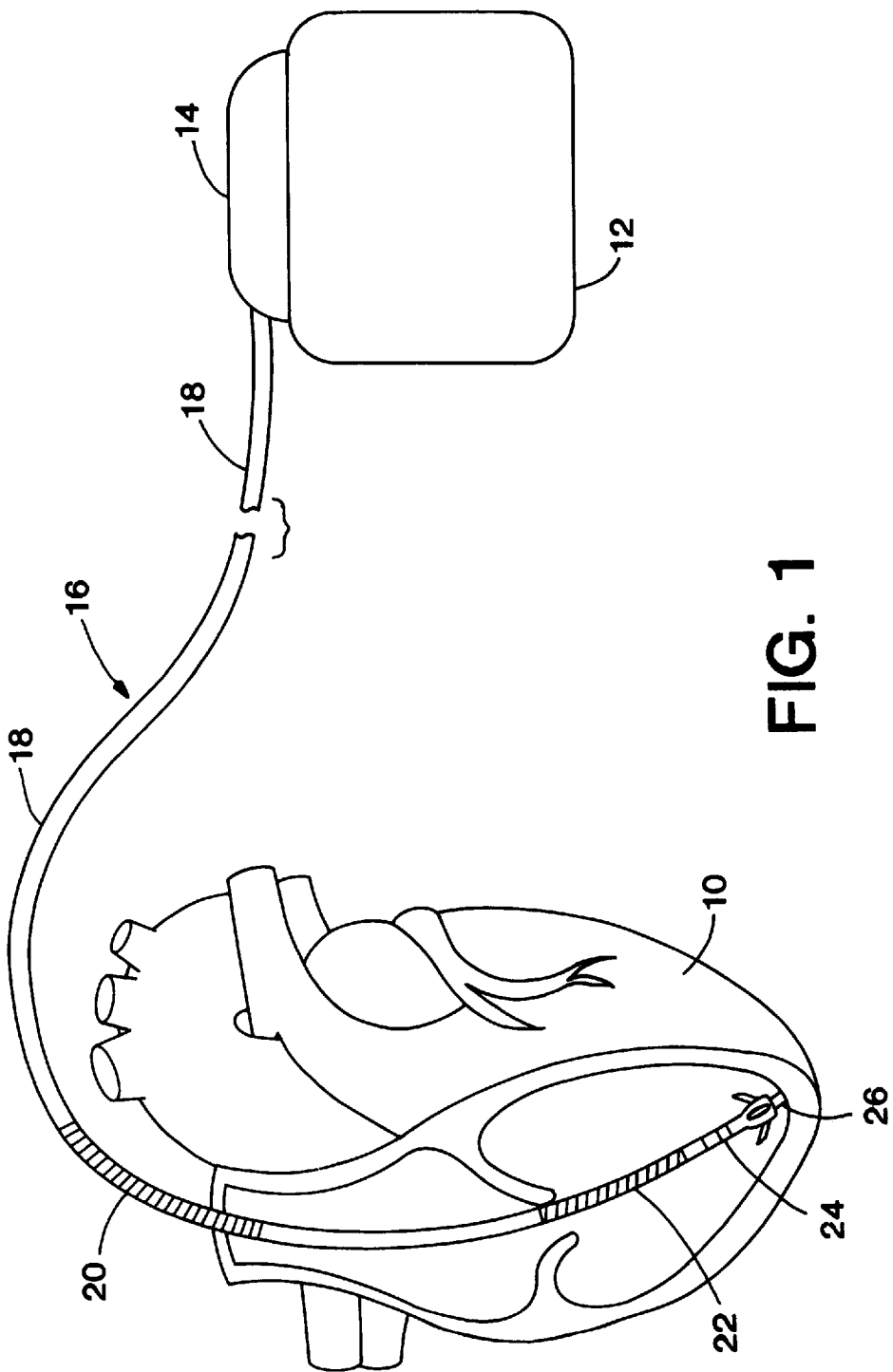
FIG. 1 illustrates an implantable pacemaker/cardioverter/ defibrillator and associated lead in which the invention is practiced.

FIG. 1 illustrates an implantable pacemaker/cardioverter/defibrillator 12, provided with a connector block 14 according to the present invention. A pacing/defibrillation lead 16 according to the present invention is shown with its proximal end and connector assembly inserted into a bore within connector block 14. The lead 16 is provided with an elongated, insulative lead body 18 which carries four electrodes, including first and second defibrillation electrodes 20 and 22 and pacing electrodes 24 and 26. The lead, thus, is provided with four insulated conductors and correspondingly carries four connector elements on the connector assembly located within the bore of connector block 14. While the invention is disclosed in the context of an implantable pacemaker/cardioverter/defibrillator, it may also usefully be employed in conjunction with other types of stimulators such as nerve and muscle stimulators, and may also be employed in conjunction with implantable electronic monitoring devices as disclosed in U.S. Pat. No. 5,331,996, issued to Bennett et al., implantable nerve and muscle stimlators and other implantable electronic devices requiring interconnection with a lead carrying electrodes, sensors or other components which must be electrically coupled to the device.

Figure 2:
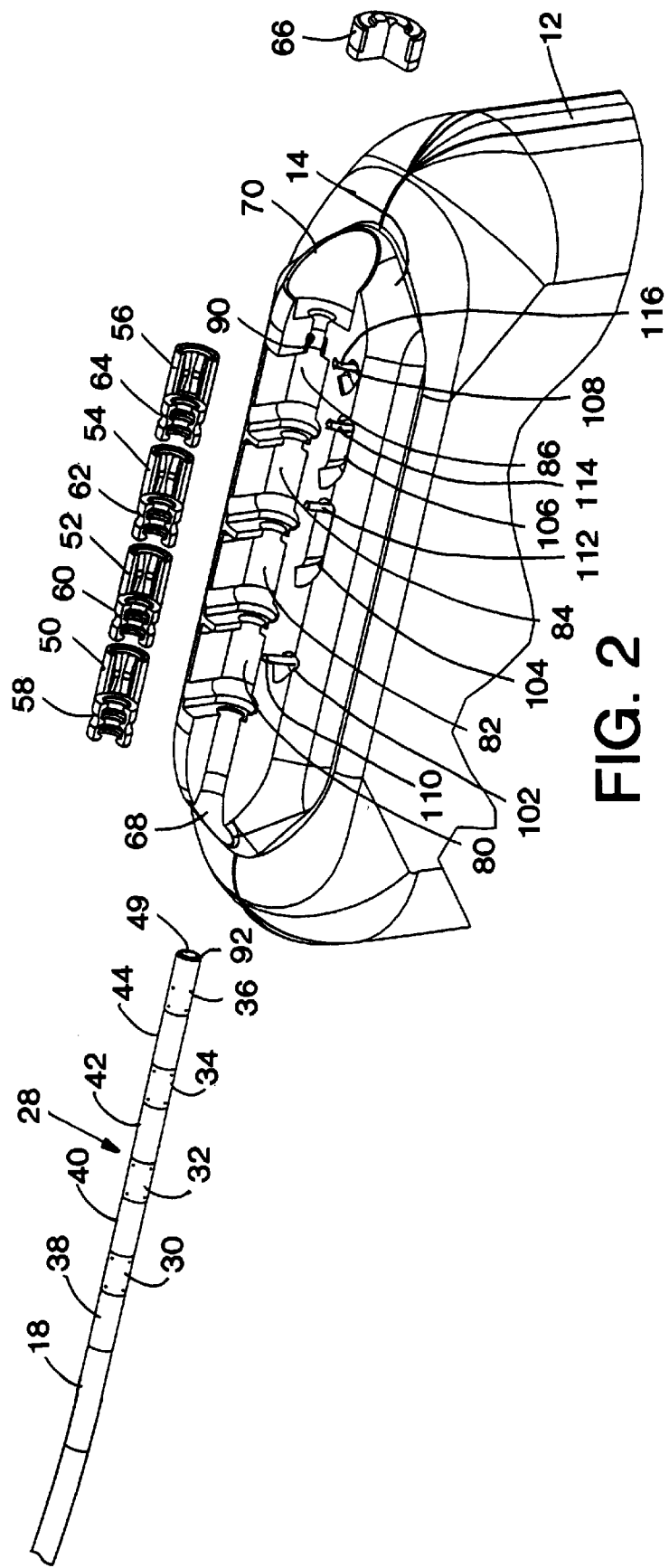
FIG. 2 is an exploded, cut-away drawing of the major components of the connector assembly of the lead and connector block of the pacemaker/cardioverter/defibrillator illustrated in FIG. 1.

FIG. 2 illustrates an exploded, cut-away view of the connector block 14 and of the components located therein, along with a perspective view illustrating the structure of the lead connector assembly 28, located at the proximal end of the lead 16, of FIG. 1. Connector assembly 28 is a rigid tubular structure carrying connector rings 30, 32, 34, and 36, each of which are coupled to one of the conductors within lead body 18. As illustrated, the connectors are all metal rings of equal diameter and the connector assembly is essentially isodiametric along that portion of the assembly carrying the connectors, allowing the size of the connector assembly 28 and connector block 14 to be minimized. However, the invention may usefully be practiced in the context of connector assemblies having non-uniform external diameters and/or connector assemblies in which the connectors do not extend around the circumference of the connector assembly, as illustrated in the above cited Daglow patent. The connector assembly also includes plastic spacers 38, 40, 42, 44 and 46, which separate the connector rings and engiage sealing rings located within the connector block 14. Spacers 38, 40, 42 and 44 are preferably fabricated of a relatively rigid plastic. Connector ring 36 is provided with a threaded bore in its proximal end, and its proximal end defines an external stop surface 92. The threaded bore 49 is employed to interconnect the connector assembly 28 with the pulling tool, described below.

The stiffness of lead body 18 adjacent connector assembly 28 need not be sufficient to apply insertion forces sufficient to insert the connector assembly 28 all the way into the bore of connector block 14 to be applied to the connector assembly, and the tensile strength of the lead body need not be greater than the required removal forces, as discussed above. The structure of the lead body may thus be chosen to optimize other lead characteristics such as flexibility and size, which otherwise might be negatively impacted if the lead body had to be capable of applying the required insertion and removal forces. Any of the various known lead body designs may be employed, including the lead body designs illustrated in U.S. Pat. No. 5,584,873, issued to Shoberg et al, U.S. Pat. No. 4,608,986, issued to Beranek et al., U.S. Pat. No. 5,324,321, issued to Polhndorf et al., U.S. Pat. No. 5,358,517 issued to Pohndorf et al. and U.S. Pat. No. 4,355,646, issued to Kallok et al., all incorporated herein by reference in their entireties.

The connector block is provided with a longitudinal bore extending between a distal opening 68 and a proximal opening 70. Intersecting this bore are a series of downwardly extending recesses 80, 82, 84 and 86 in which electrical connectors 50, 52, 54, and 56 and sealing rings 58, 60, 62 and 64 are to be inserted. It should be noted that a sealing ring is provided to seal the connector assembly adjacent each end of the bore through the connector block 14, to prevent fluid infiltration through distal opening 68. A pierceable sealing grommet 66 is located in the proximal opening 70 of the connector block, and seals the bore against ingress of fluids after removal of the pulling tool as described below.

The sealing rings 58, 60, 62 and 64, and grommet 66 may be molded silicone rubber or other elastomeric material, and are of a type conventionally used in conjunction with present implantable pacemakers and cardioverters. Electrical connectors 50, 52, 54, and 56, each take the form of a cylindrical ferrule containing a cylindrical, inwardly biased multi-beam spring element of the sort illustrated in U.S. Pat. No. 5,207,218 issued to Carpentier et al., incorporated by reference in its entirety herein. These electrical connector assemblies are also conventional elements, corresponding to connectors presently employed in conjunction with implantable pacemakers. Connector block 14 is shown mounted to the upper portion of the implantable pacemaker/cardioverter/defibrillator 12 illustrated in FIG. 1.

Electrical connectors 50, 52, 54, and 56 are interconnected with the implantable defibrillator 12 by means of feed-through wires 110, 112, 114, and 116, which extend upward from the defibrillator 12 through apertures 102, 104, 106, and 108, respectively. In the illustration, the connector pins are shown substantially shorter than their actual length. In practice, after insertion of connectors 50, 52, 54, and 56 into recesses 72, 74, 76, and 78, feed-through wires 110, 112, 114, and 116 may be bent over and into contact with the upper portions of connectors 50, 52, 54, and 56, and coupled thereto by means of laser welding. All recesses in the connector block 14 may thereafter be backfilled with silicone rubber or other elastomeric material, to seal the connector block assembly.

Figure 3:
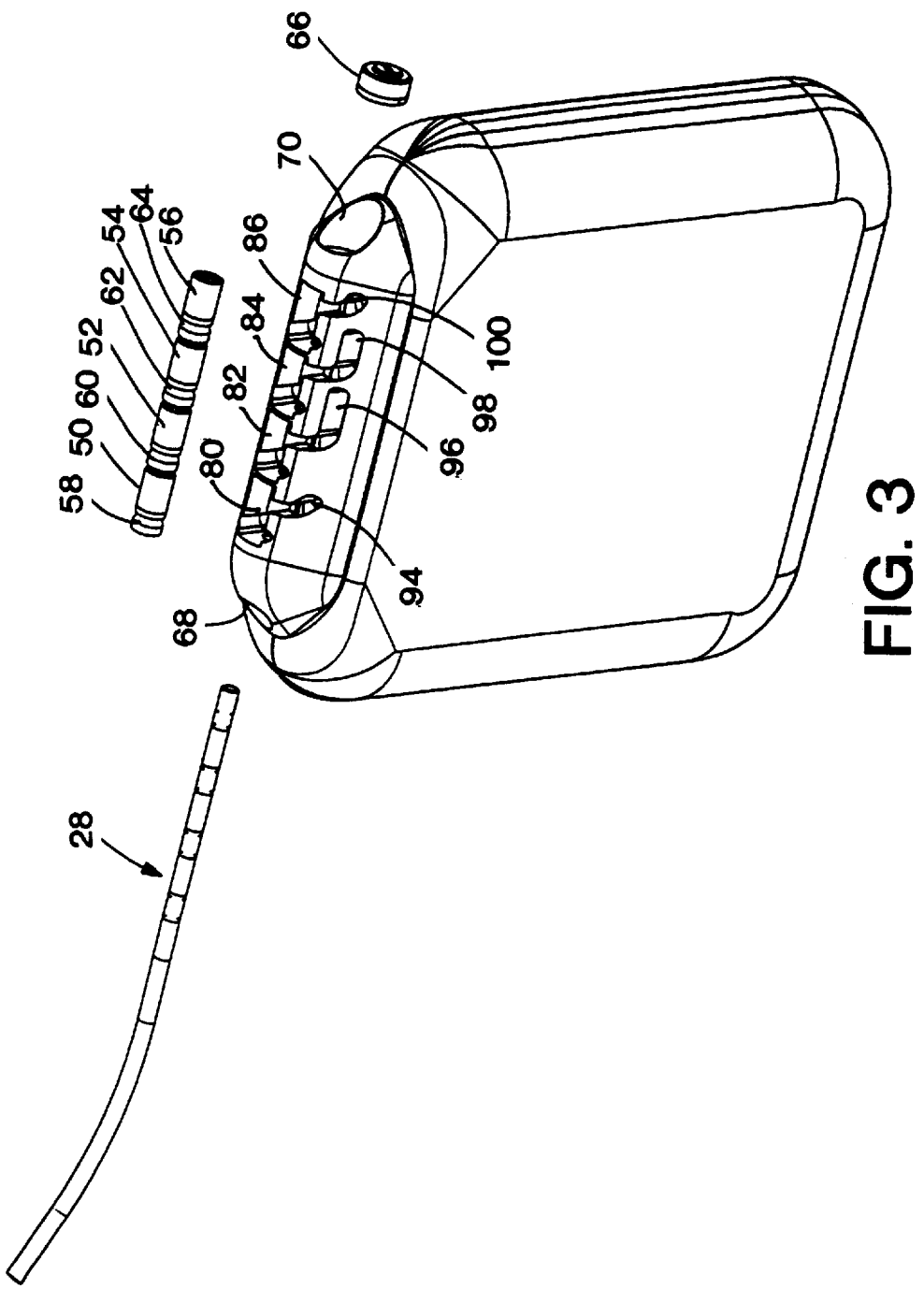
FIG. 3 is a perspective view of the major components of the connector assembly of the lead and the connector block of the pacemaker/cardioverter/defibrillator illustrated in FIG. 1.

FIG. 3 illustrates the major components of the electrical connector system according to the present invention in perspective view. Connector block 14 is shown attached to the pacemaker/cardioverter/defibrillator 12. In this view, it can be seen that recesses 72, 74, 76, and 78 which are to receive electrical connectors 50, 52, 54, and 56, are provided with laterally extending slots 94, 96, 98, and 100. Slots 94, 96, 98, and 100 are in communication with apertures 102, 104, 106, and 108, illustrated in FIG. 2. The feed-through wires 110, 112, 114, and 116 illustrated in FIG. 2 are bent over in slots 94, 96, 98, and 100, and into contact with electrical connectors 50, 52, 54, and 56 after their insertion into the corresponding recesses, and the feedthrough wires and associated electrical connectors are thereafter welded to one another. After assembly, all of the recesses, as noted above, are filled flush with silicone rubber or other plastic material in order to seal the connector block against fluid ingress. All other labeled elements of FIG. 3 correspond to identically labeled elements in FIG. 2.

Figure 4:
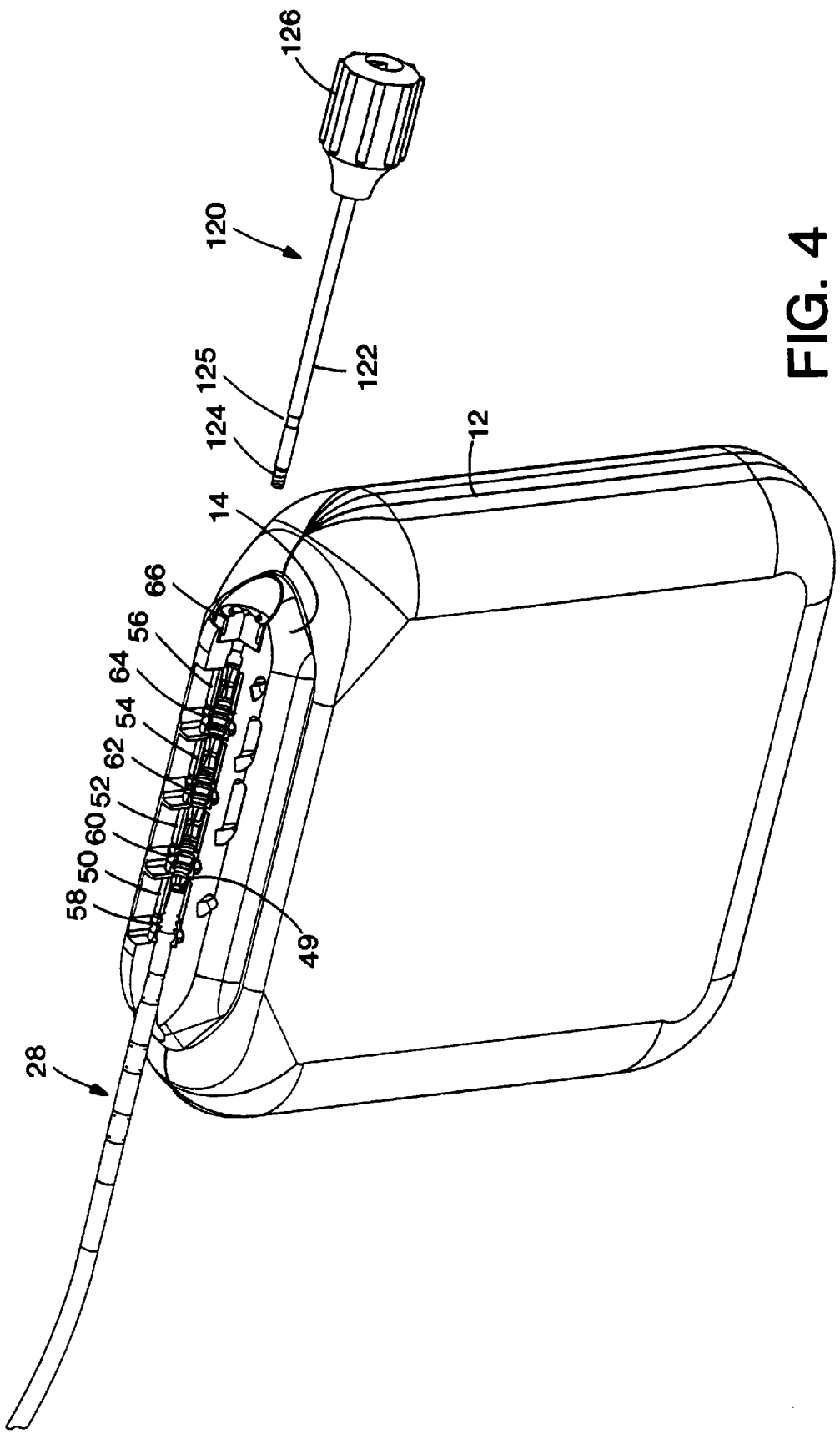
FIG. 4 is a cut-away view through the connector block of the pacemaker/cardioverter/defibrillator illustrated in FIG. 1, illustrating preliminary insertion of the proximal portion of the connector assembly on the lead into the connector block, and also illustrating a first embodiment of the pulling tool.

FIG. 4 is a cut-away view illustrating the connector assembly 28 of the lead 16, partly inserted into the connector block 14, mounted to pacemaker/cardioverter/defibrillator 12. In this view, sealing rings 58, 60, 62 and 64, and electrical connectors 50, 52, 54, and 56, are shown located in their corresponding recesses within the connector block, such that the central lumens through each of these components are axially aligned with the proximal and distal openings 68 and 70 of the bore through the connector block 14. Also illustrated is a first embodiment of a pulling tool 120, which comprises a rod 122, carrying a threaded distal portion 124 and a knob 126 located at the proximal end of the tool 120. The threaded section 124 of rod 122 is sized to engage with the threaded bore 49 of connector ring 36, after insertion through sealing grommet 66. A visual; indicator 125 is provided on the rod 122, located such that when the tool has been used to pull connector assembly 28 to its fully inserted position, the indicator is visible outside of sealing grommet 66.

Figure 5:
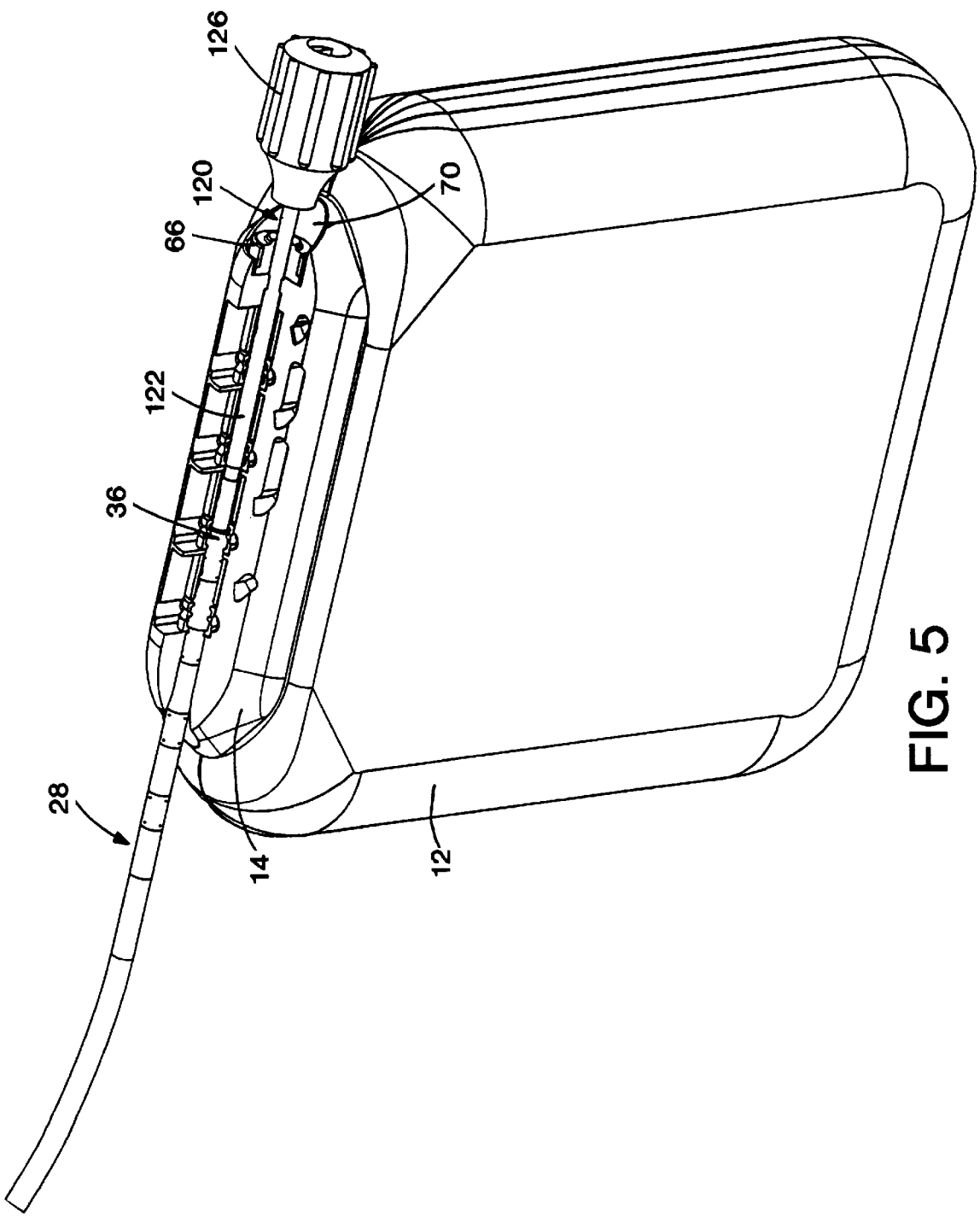
FIG. 5 is a cut-away view illustrating the pulling tool attached to the proximal end of the lead connector assembly.

FIG. 5 illustrates a cut-away view through connector block 14, illustrating the pulling tool 120 inserted through the proximal opening 70, through sealing grommet 66 and engaged with the threaded recess in connector ring 36 at the proximal end of the lead connector assembly 28. Connector assembly 28 has been inserted slightly into connector block 14 to a first position, by grasping the distal portion of the connector assembly and pushing the proximal portion of the connector assembly into the connector block. Knob 126 is used to rotate rod 122 to screw the threaded portion 124 into member 48 to accomplish interconnection with the connector assembly 28. Rod 122 has a length sufficient to extend proximally out the proximal opening 70, while engaged with the connector assembly 28 in this first position, so that the knob 126 can be grasped manually to pull connector assembly 28 proximally to a fully inserted position.

Figure 6:
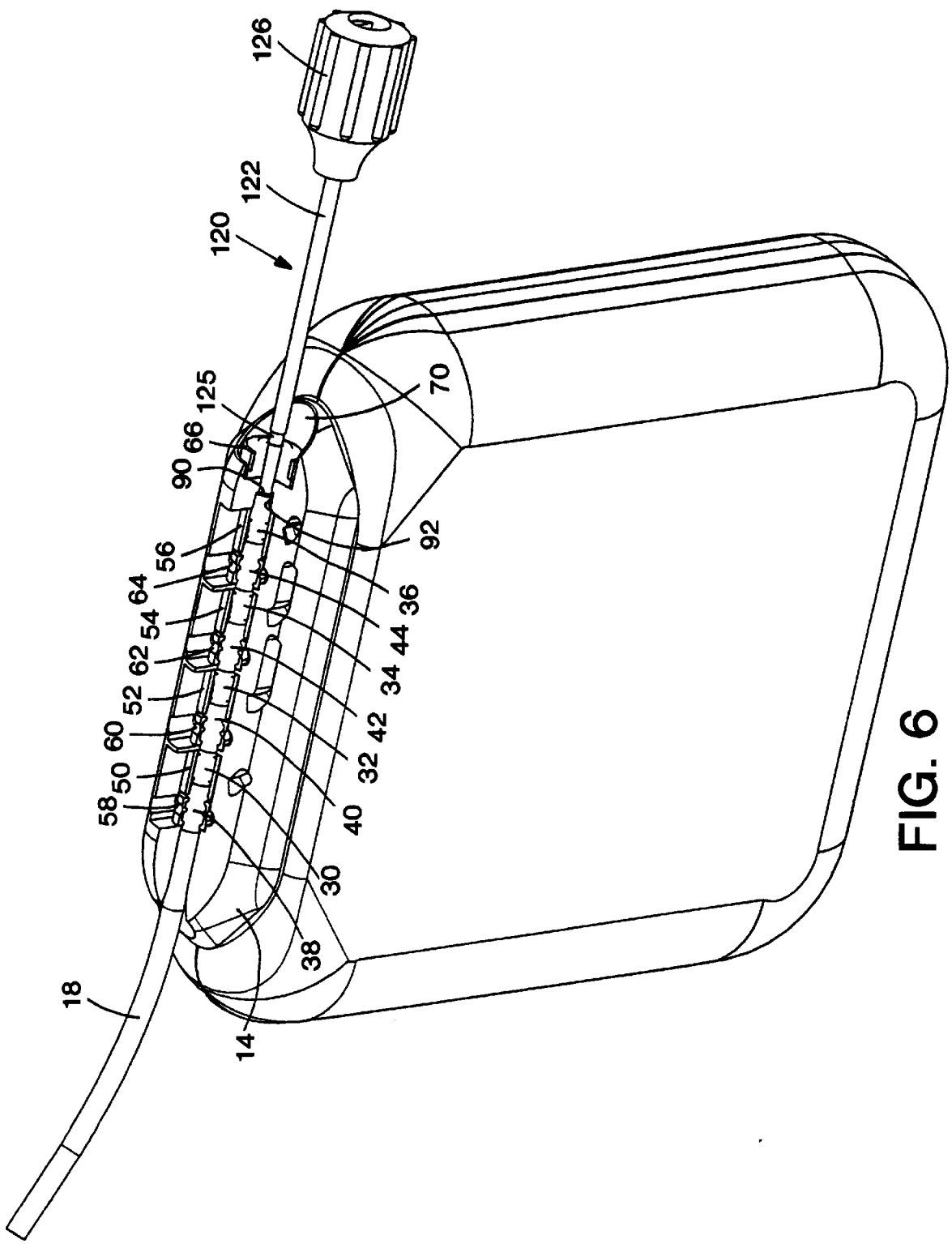
FIG. 6 is a cut-away view illustrating the connector assembly of the lead after it has been pulled into its correct position in the connector block of the defibrillator illustrated in FIG. 1 by means of the pulling tool.

FIG. 6 is a cut-away view showing the lead connector 28 fully inserted into the bore of connector block 14. In this view, it can be seen that connector rings 30, 32, 34, and 36 are located within and arc frictionally engaged with electrical connectors 50, 52. 54, and 56. The plastic spacers 38, 40, 42 and 44 are each engaged with corresponding sealing rings 58, 60, 62 and 64. Knob 126 is used to pull tool 120 proximally until the stop surface 92 on member connector ring 36 meets and engages a corresponding internal stop surface 90, located slightly inward of the proximal opening 70 of the bore through connector block 14. Other mechanical mechanisms providing an insertion stop may, of course, be substituted.

Figure 7:
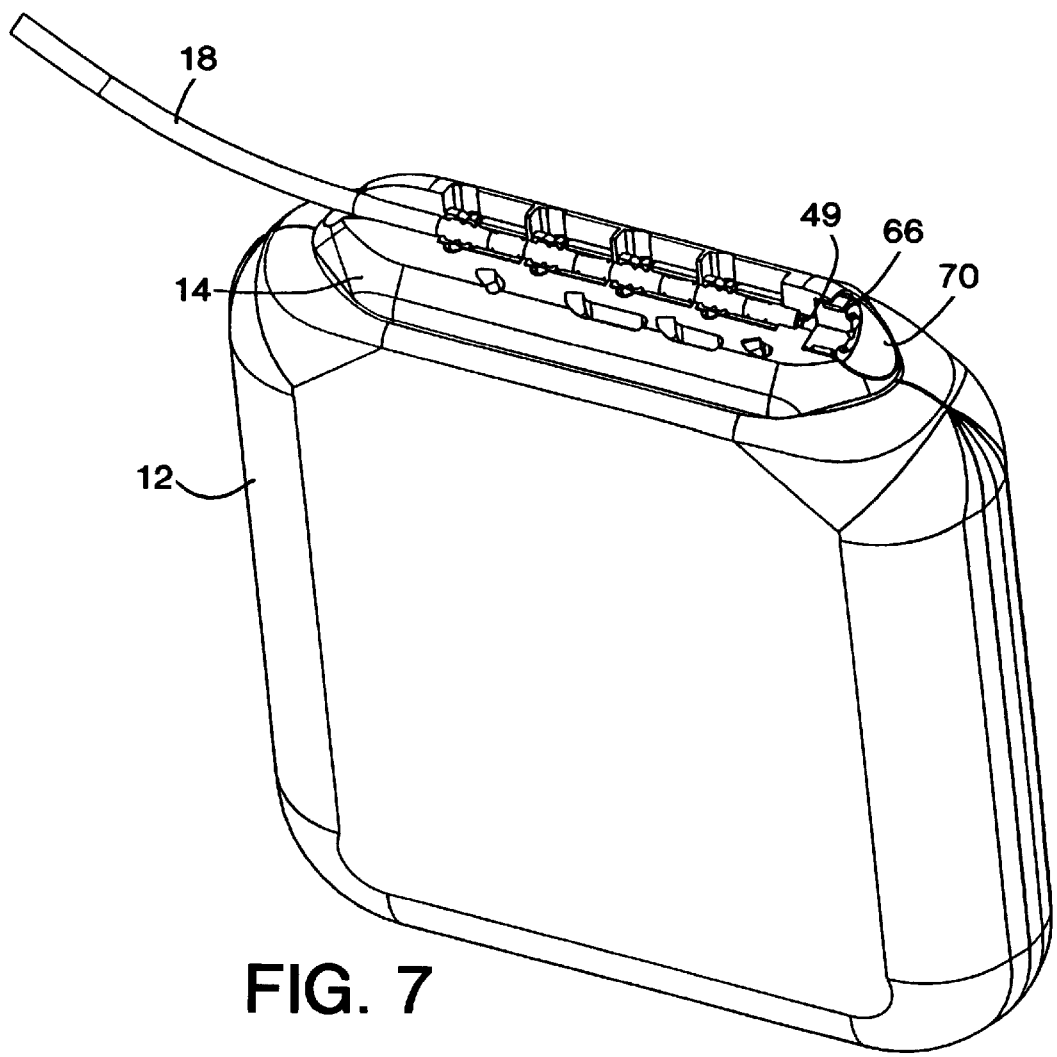
FIG. 7 is a cut-away view of the connector assembly of the lead fully inserted in the connector block of the pacemaker/cardioverter/defibrillator illustrated in FIG. 1, after removal of the pulling tool.

FIG. 7 is a cut-away view illustrating electrical assembly 28 of the lead fully inserted into connector block 14, after removal of the pulling tool. Sealing grommet 66 seals the proximal opening 70 after removal of pulling tool 120. In this form, the device is ready for implantation. It should be noted that in some embodiments, the threaded bore within connector ring 36 may be aligned with an internal lumen through the lead body, allowing passage of a stylet through the lead body. In this case, the present invention has an additional benefit of allowing insertion of the stylet into the lead body, through the sealing grommet 66, after interconnection of the lead and the pacemaker/cardioverter/defibrillator. This additional benefit of the invention allows for repositioning of the lead without disconnection of the lead.

To remove the lead from the connector block 14, the insertion tool 120 would simply be pushed through grommet 66, reattached to connector ring 36, and used to push the lead distally, out of the connector block 14 until the connector assembly 28 can be grasped by the physician. The tool 120 is then disconnected from the connector assembly 28 and removed from the connector block 14, after which the lead may be pulled completely out of the connector block, in a reversal of the steps described above for insertion of the lead into the connector block.

While the embodiment discussed above relies on the frictional engagement of the sealing rings, and electrical connectors in the connector block with the connector assembly 28 to retain the lead in the fully inserted position, in some embodiments of the invention an additional mechanical locking mechanism might be provides. This additional locking mechanism may take the form of a set-screw type electrical connector for engaging with one of the connector rings, a mechanical mechanism for engaging one of the insulative spacers, such as in U.S. Pat. No. 4,860,750, issued to Frey et al., incorporated herein by reference in its entirety or an alternative mechanical or electrical connector providing an interlock, as in U.S. Pat. No. 5,489,225 issued to Julian, the above cited Daglow patent. U.S. Pat. No. 5,257,622, issued to Hooper et al. or U.S. Pat. No. 5,252, 090, issued to Giurtino et al, all incorporated by reference in their entireties. An additional alternative, not illustrated, might employ a locking screw engaging threaded bore 49 to retain the connector assembly in the connector block as in U.S. Pat. No. 3,649,367 issued to Purdy and incorporated herein in its entirety. Such a locking screw might include a seal and be substituted for sealing grommet 66 as a mechanism for sealing the proximal opening 70 after removal of the tool 120 or alternatively a fifth insulative spacer at the proximal end of connector assembly 28 might engage a fifth set of sealing rings as mechanism for sealing the proximal opening 70, with the locking screw engaging a threaded bore in the proximal end of the fifth insulative spacer.

Figure 8:
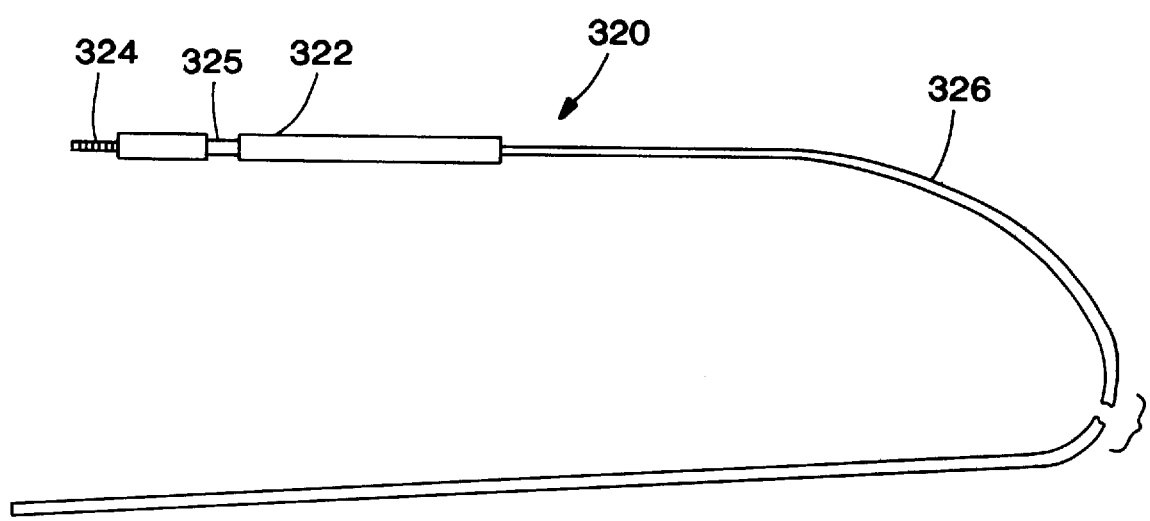
FIG. 8 is a plan view of a combined pulling tool/ extension.

FIG. 8 illustrates a pulling tool/extension 320. In this embodiment, the tool is provided with a rod 322 having a threaded section 324 corresponding to rod 122 and threaded section 124 of the tool 120 illustrated in the figures above. However, rather than employing a knob on the proximal end, it is provided with an elongated flexible wire extension 326, which is sized so that the total length of the tool 320 is longer than the length of the guide catheter 250, illustrated in FIG. 9. A visual indicator 325 is provided on rod 322, corresponding to the visual indicator 125 of tool 120, illustrated above. Before or after placement of the lead to the desired location as illustrated in FIG. 9, threaded segment 324 is screwed into a corresponding threaded bore in the proximal end of the lead connector assembly 228, illustrated in FIG. 9.

Figure 9:
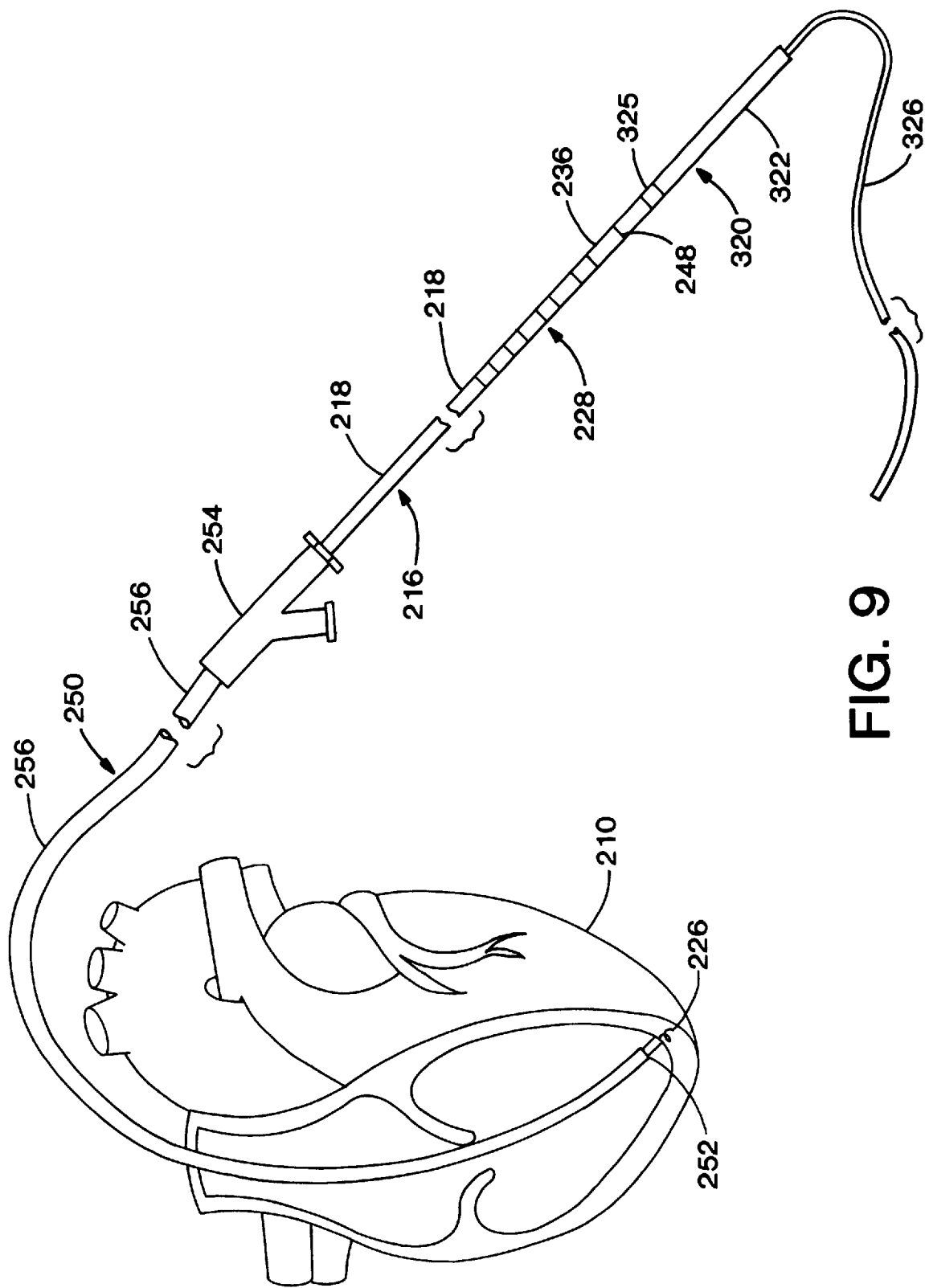
FIG. 9 is an illustration of the implantation of a pacemaker/cardioverter/defibrillator lead by means of a guide catheter, showing initial placement of the lead in the heart.

FIG. 9 illustrates the insertion of a defibrillation lead of the type in which the lead is guided to a desired location through a guide catheter or extended introducer sheath 250. Guide catheter 250 is first inserted in the heart so that its distal end 252 is adjacent the desired location for the distal end of the lead 216. Lead 216 is then advanced through fitting 254 on the proximal end of the guide catheter 250 and through the internal lumen through elongated tubular body 256 of the guide catheter until the distal end of lead 21 8 reaches the desired location. As illustrated, the distal end of the lead 216 is provided with a helical electrode 222 which may then be screwed into heart tissue by rotation of the lead body 218.

In the embodiment illustrated, connector assembly 228 is isodiametric to lead body 216, and in any case is sized so that it may freely pass through the fitting 254 at the proximal end of guide catheter 250. This allows guide catheter 250 to be removed over the lead 216, without requiring splitting or other disassembly of the catheter. A threaded bore corresponding to bore 49 illustrated in FIG. 2, is located in connector ring 236 at the proximal end of connector assembly 228. Pulling tool/extension 320 is shown attached to the proximal end of connector assembly 228 by engagement with the threaded bore in connector ring 236. All numbered elements of tool 320 correspond to those illustrated in FIG. 8, discussed above.

Figure 10:
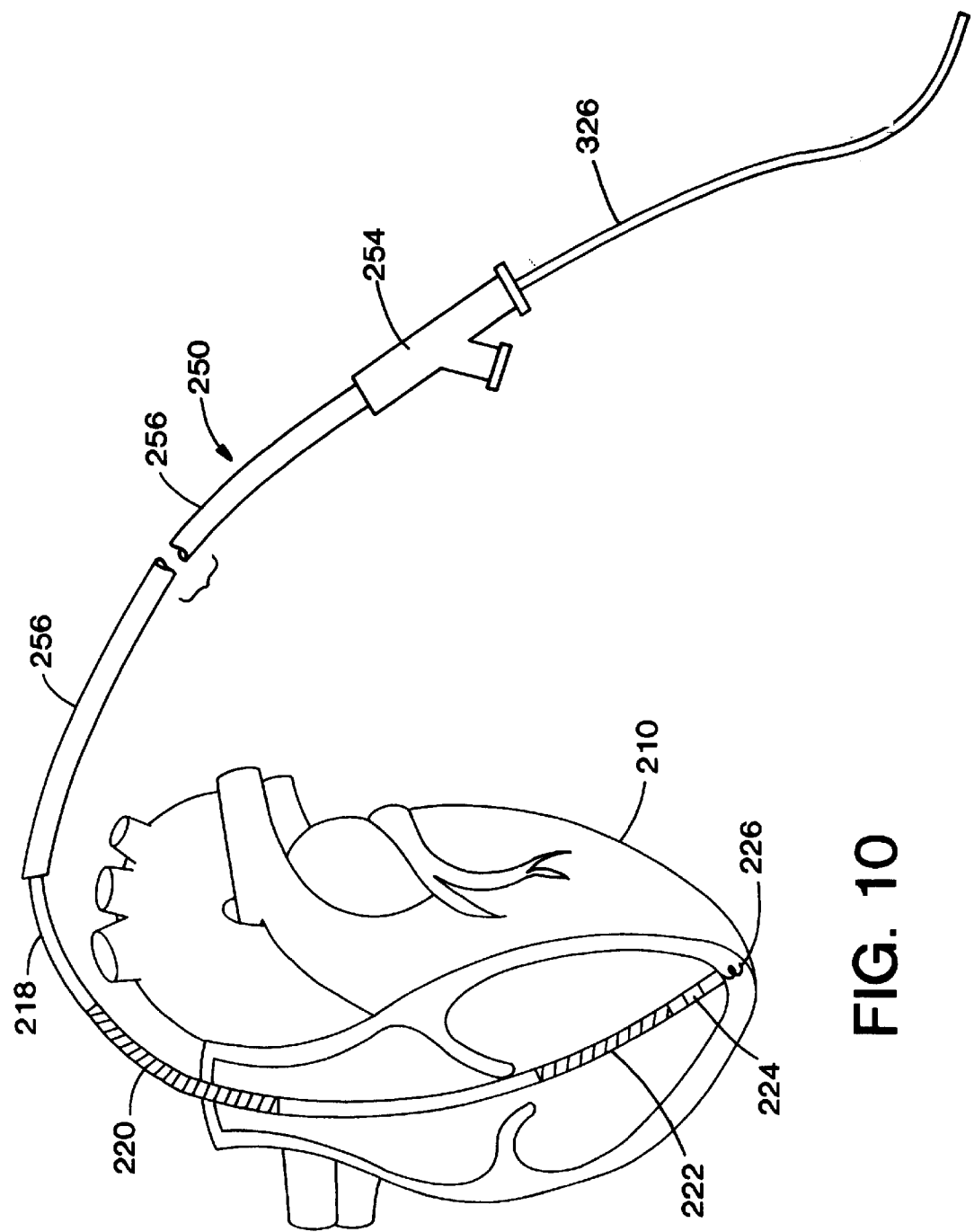
FIG. 10 is a figure illustrating the removal of the guide catheter over the lead illustrated in FIG. 8, facilitated by means of the pulling tool/extension illustrated in FIG. 9.

FIG. 10 shows the process of the removal of the guide catheter 250 over lead 216, after attachment of the pulling tool/extension 320. In this view, guide catheter 250 has been moved proximally so that the connector assembly of the lead 216 is located within the tubular body 256 of the guide catheter. The wire extension 326 of tool 320 extends proximally out of fitting 254, so that it may be grasped by the physician as the guide catheter is pulled proximally, without disturbing the position of the lead 218 within the heart and the vascular system. Lead 216, like lead 16 of FIG. 1, is provided with first and second defibrillation electrodes 220 and 222 and is provided with first and second pacing electrodes 224 and 226.

After the proximal end of guide catheter 250 passes the connector assembly 228 of lead 216, the connector assembly of the lead may be grasped by the physician, and thereafter either of two things may occur. The pulling tool/extension 320 may simply be unscrewed from the connector block 228 of the lead, and discarded along with the guide catheter 250. In such case, a pulling tool corresponding to tool 120, as illustrated in FIG. 2, would be employed to insert the lead into the connector block of pacemaker/cardioverter/defibrillator 12, as illustrated in FIG. 1. Alternatively, the pulling tool/extension 320 may be left attached to the connector assembly 228, and used to pull the connector assembly 228 into the connector block of the defibrillator.

Figure 11:
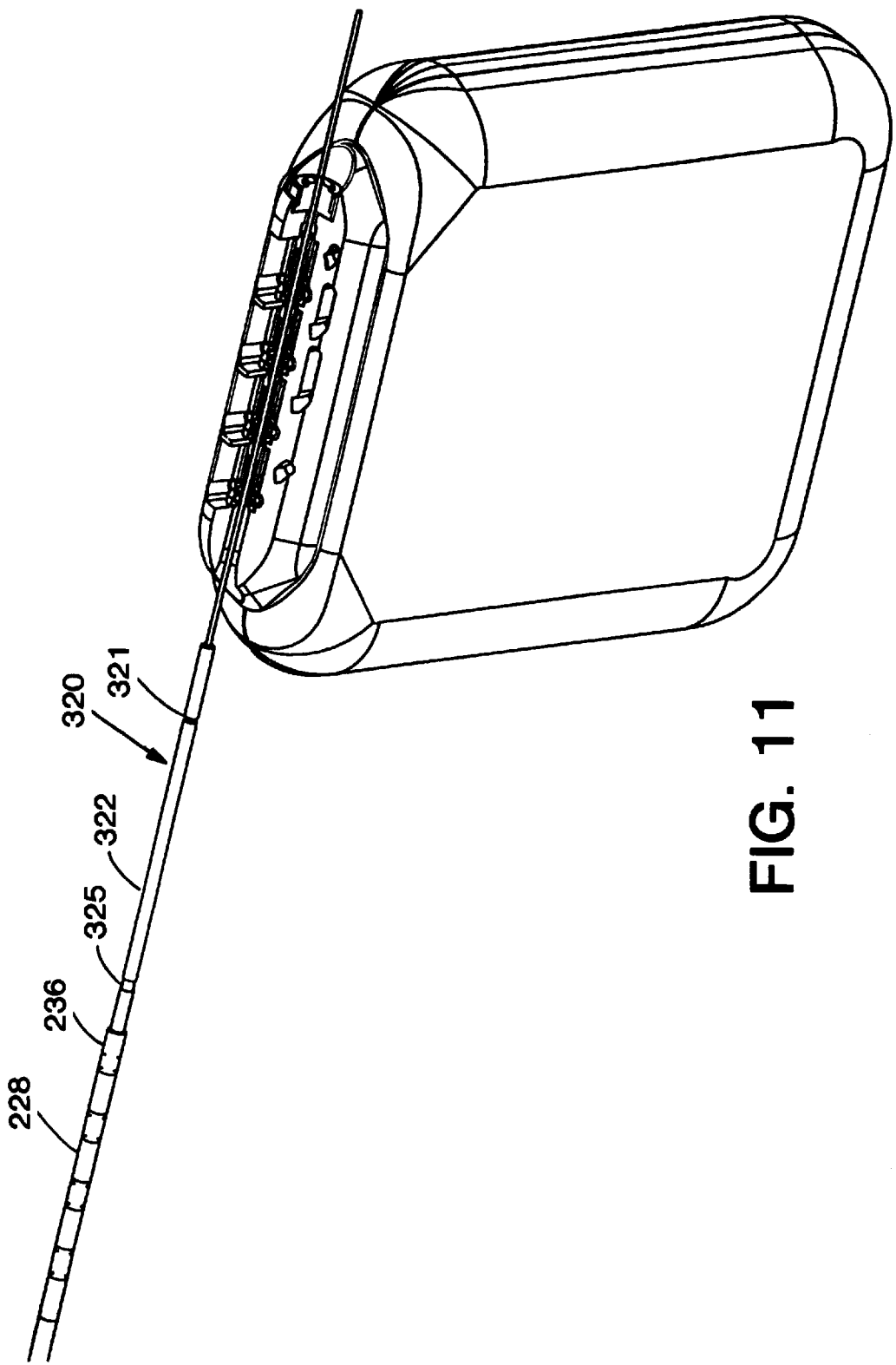
FIG. 11 is a cut-away view illustrating the insertion of the pulling tool/extension of FIG. 9 through the connector block of the pacemaker/cardioverter/defibrillator illustrated in FIG. 1, while coupled to the lead illustrated in FIGS. 8 and 10.

FIG. 11 is a cut-away view illustrating the connector block 14 in conjunction with the electrical connector assembly 228 of lead 216, to which the pulling tool/extension 320 remains attached. The extension 326 is shown inserted through the bore through connector block 14, exiting the proximal opening 70. Prior to insertion of the extension 326, it may be trimmed to a shorter length, if desired, by means of snipping or cutting the wire. Alternatively, the wire extension 326 may be provided with a circumferential groove to allow the wire to be snapped off at a predetermined location. The extension 326 is used to pull the lead connector assembly 228 into position within connector block 14 in precisely the fashion described above in conjunction with the preceding figures. The pulling tool/extension 320 is then removed and discarded.

The embodiments of the invention illustrated above are intended to be exemplary of the type of the device in which the invention may be practiced. In conjunction with these embodiments, a connector assembly for use on the lead which takes the form of an isodiametric, essentially cylindrical connector assembly having four electrical connectors is disclosed. However, the present invention may also be usefully practiced in conjunction with a lead connector assembly which has more or less electrical connectors and/or is of stepped diameter, rather than isodiametric. In addition, the embodiments illustrated above employ a connector block which contains the sealing rings required to seal between the electrical connectors on the lead connector assembly and to seal the proximal end distal apertures of the lumen through the connector block. This construction is believed preferable, in conjunction with an isodiametric lead system, as if sealing rings were provided on the lead, the more proximal the sealing rings would have to pass through electrical connectors within the lead body which were intended to engage connector rings of a diameter less than the diameter of the sealing rings, which would in most cases lead to mechanical damage to the sealing rings. However, in the context of an embodiment employing stepped diameters for the connector assembly on the lead, such that the outer diameter of the connector pins and rings decrease from one connector pin or ring to the next pin or ring proximal to it, it is believed that sealing rings on the connector assembly may also be usefully employed.

In addition, the illustrated embodiments employ frictional electrical connectors in which the frictional engagement means, e.g., the spring member, is located permanently within the connector block. However, it is believed that the invention can also be usefully practiced in the context of a lead as described in the Peers-Trevarton patent, cited above, in which the frictional interconnection or spring members are located on the lead connector assembly. In such an embodiment, the sealing rings may also be located on the lead body, intermediate the electrical connectors as illustrated in the above cited patent, and the connector block may be provided with essentially an isodiametric bore, in reversal of the elements of the invention as illustrated in the embodiments disclosed above.

Finally, as noted above, it is believed that the invention can also be practiced in embodiments which employ a set screw or other additional mechanism for retaining the lead connector assembly within the bore of the connector assembly within the bore of the connector block. As such, the above disclosure should be considered exemplary rather than limiting with regard to the scope of the claims that follow.

In conjunction with the above disclosure, we claim:

1. An implantable medical device system comprising an implantable electronic device having a first plurality of electrical connectors and an associated electrical lead having a second plurality of electrical connectors engagable with said first plurality of electrical connectors, wherein:

said lead comprises an elongated lead body having proximal and distal ends and having a connector assembly mounted to the proximal end of said lead body and having said second plurality of electrical connectors mounted along said connector assembly, said connector assembly further comprising a first mechanical connector; and said device is provided with a connector block having a bore extending therethrough from a proximal opening to a distal opening, sized to receive said connector assembly and having said first plurality of electrical connectors located along said bore such that on full insertion of said connector assembly into said connector block through the distal opening of the bore of said connector block, said second plurality of connectors engage said first plurality of connectors; and wherein said system further comprises:

pulling tool means for pulling said connector assembly proximally in said bore of said connector block from a first position in which said connector assembly is not fully inserted in said connector block to a second position in which said connector assembly is fully inserted in the bore of said connector block, said pulling tool means having a second mechanical connector at a distal end thereof engagable with said first mechanical connector and an elongated member sized for insertion into the proximal opening of the bore of said connector block and extending proximally from said second mechanical connector for a length sufficient length to extend proximally out of the proximal opening of the bore of said connector block when said connector assembly is in said first position and said second mechanical connector is engaged with said first mechanical connector; whereby said elongated member may be grasped and pulled proximally to pull said connector assembly from said first position to said second position.

2. A system according to claim 1 wherein said second plurality of connectors are arranged linearly along said connector assembly.

3. A system according to claim 1 or claim 2, further comprising means for sealing the proximal and distal openings of the bore of said connector block when said connector assembly is fully inserted in said connector block.

4. A system according to claim 1 or claim 2 wherein said first plurality of connectors comprise means for frictionally engaging said second plurality of connectors.

5. A system according to claim 1 or claim 2 wherein said first plurality of connectors comprise means for frictionally resisting proximal movement of said connector assembly to said second position.

6. A system according to claim 1 or claim 2 further comprising means for sealing between adjacent ones of said first plurality of electrical connectors.

7. A system according to claim 6 wherein said sealing means comprise means for frictionally resisting proximal movement of said connector assembly to said second position.

8. A system according to claim 6 wherein said sealing means comprise resilient sealing rings.

9. A system according to claim 8 wherein said sealing rings are mounted within said connector block.

10. A system according to claim 1 or claim 2 wherein said first and second mechanical connectors are provided with internal and external screw threads, respectively.

11. A system according to claim 1 or claim 2 wherein one of said first and second pluralities of connectors comprises connectors having conductive spring means for engaging the other of said first and second pluralities of connectors.

12. A system according to claim 1 or claim 2 wherein one of said first plurality of connectors comprises connectors having conductive spring means for engaging said second plurality of connectors.

13. A system according to claim 1 or claim 2 wherein said connector assembly is generally cylindrical and isodiametric from one of said second plurality of connectors to an adjacent one of said second plurality of connectors.

14. A system according to claim 1 or claim 2 further comprising insertion stop means for preventing proximal movement of said connector assembly beyond said second position.

15. A system according to claim 1 or claim 2, further comprising an elongated introducer catheter having an elongated lumen through which said lead body may pass and wherein said elongated member of said pulling tool means has a length greater than said introducer catheter.

16. A system according to claim 1 or claim 2 wherein the elongated member of the pulling tool means comprises a visual indicator means for indicating that said connector assembly is fully inserted in said connector block.

17. A method of interconnecting an implantable medical device having a first plurality of electrical connectors and an associated electrical lead having a second plurality of electrical connectors engagable with said first plurality of electrical connectors, said lead comprising an elongated lead body having proximal and distal ends and having a connector assembly mounted to the proximal end of said lead body and having said second plurality of electrical connectors mounted along said connector assembly, said device provided with a connector block having a bore extending therethrough from a proximal opening to a distal opening, sized to receive said connector assembly and having said first plurality of electrical connectors located along said bore such that on full insertion of said connector assembly into said connector block through the distal opening of the bore of said connector block, said second plurality of connectors engage said first plurality of connectors; said method comprising:

inserting a pulling tool into said bore of said connector block so that it extends through said proximal opening and mechanically engaging it with said connector assembly;

pulling said connector assembly by moving said pulling tool proximally, from a first position in which said connector assembly is not fully inserted in said connector block to a second position in which said connector assembly is fully inserted in the bore of said connector block.

18. A method of implanting an electrical lead, said lead comprising an elongated lead body having proximal and distal ends and having a connector assembly mounted to the proximal end of said lead body and having a second electrical connector mounted to connector assembly, said medical device provided with a connector block having a bore extending therethrough from a proximal opening to a distal opening, sized to receive said connector assembly and having said first electrical connector located along said bore such that on full insertion of said connector assembly into said connector block through the distal opening of the bore of said connector block, said first and second electrical connectors engage one another, said method comprising:

advancing said lead to a desired location in a patient's body, mechanically engaging a pulling tool with said connector assembly; inserting said pulling tool into said bore of said connector block so that it extends out said proximal opening of said connector block; and pulling said connector assembly by moving said pulling tool proximally, from a first position in which said connector assembly is not fully inserted in said connector block to a second position in which said connector assembly is fully inserted in the bore of said connector block.

19. A method according to claim 18 wherein said advancing step comprises advancing said lead through a catheter to said desired location and wherein said inserting step comprises inserting a pulling tool having means for mechanically engaging said connector assembly and an elongated member extending proximally from said engaging means, further comprising: and sliding said catheter proximally over said elongated member while said pulling tool is engaged with said connector assembly while holding said pulling tool to retain said lead in said desired location.

20. A method of implanting an electrical lead and connecting it to an implantable medical device having a first electrical connector, said lead comprising an elongated lead body having proximal and distal ends and having an electrical connector assembly having a second electrical connector mounted to the proximal end of said lead body, said method comprising:

advancing said lead through a catheter to a desired location in a patient's body, mechanically engaging with said connector assembly a tool having means for mechanically engaging said connector assembly and an elongated member extending proximally from said engaging means;

sliding said catheter proximally over said elongated member to remove it from said lead while said tool is engaged with said connector assembly and while holding said pulling tool to retain said lead in said desired location; and coupling said first and second electrical connectors.

* * * * *

UNITED STATES PATENT AND TRADEMARK OFFICE
CERTIFICATE OF CORRECTION

PATENT NO. : 5,843,141

DATED : December 1, 1998

INVENTOR(S) : Bischoff et al

It is certified that error appears in the above-identified patent and that said Letters Patent is hereby corrected as shown below:

| | |
|---|---|
| Col. 10, Line 59: | "for a length sufficient length" should be "for a sufficient length" |
| page 17, Line 26: | "for a length sufficient length" should be "for a sufficient length" |
| Cover Sheet | "Bonner D. Bonner" should be "Matthew D. Bonner" |
| Cover Sheet | "Medronic" should be "Medtronic" |

Signed and Sealed this

Twenty-second Day of May, 2001

Attest:

NICHOLAS P. GODICI

*Attesting Officer*   *Acting Director of the United States Patent and Trademark Office*